(12) United States Patent
Bunch et al.

(10) Patent No.: US 11,751,986 B2
(45) Date of Patent: Sep. 12, 2023

(54) PACKAGING SYSTEM FOR URETERAL STENT

(71) Applicant: Cook Medical Technologies LLC, Bloomington, IN (US)

(72) Inventors: Kristen M. Bunch, Bloomington, IN (US); Jonathan Sheets, Bloomington, IN (US); James B. Shively, II, Ellettsville, IN (US); Nathan P. Killey, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 351 days.

(21) Appl. No.: 16/727,425

(22) Filed: Dec. 26, 2019

(65) Prior Publication Data
US 2020/0214820 A1 Jul. 9, 2020

Related U.S. Application Data

(60) Provisional application No. 62/788,414, filed on Jan. 4, 2019.

(51) Int. Cl.
*A61F 2/00* (2006.01)
*A61F 2/04* (2013.01)

(52) U.S. Cl.
CPC ...... *A61F 2/0095* (2013.01); *A61F 2002/048* (2013.01)

(58) Field of Classification Search
CPC ............ A61F 2/0095; A61F 2002/048; A61M 25/002
USPC ....................................... 206/438, 363, 63.3
See application file for complete search history.

(56) References Cited

U.S. PATENT DOCUMENTS

| | | | | |
|---|---|---|---|---|
| 4,262,800 A | * | 4/1981 | Nethercutt | A61B 50/30 206/478 |
| 4,713,059 A | * | 12/1987 | Bickelhaupt | A61M 25/0113 242/588.6 |
| 5,099,994 A | * | 3/1992 | Kalinski | A61B 17/06133 206/409 |
| 5,271,495 A | * | 12/1993 | Alpern | A61B 17/06133 206/380 |
| 5,533,611 A | * | 7/1996 | Bordighon | A61B 17/06138 206/388 |

(Continued)

FOREIGN PATENT DOCUMENTS

| | | |
|---|---|---|
| CN | 102202595 A | 9/2011 |
| EP | 2 647 402 A1 | 9/2013 |
| EP | 3 342 444 A1 | 4/2018 |

OTHER PUBLICATIONS

Search Report and Written Opinion for PCT/US2019/068718, dated May 8, 2020, 19 pp.

(Continued)

*Primary Examiner* — Steven A. Reynolds
(74) *Attorney, Agent, or Firm* — Crowell & Moring LLP

(57) ABSTRACT

A packaging system for use with a ureteral stent having an elongated shaft extending between a proximal end portion and a distal end portion may include a tray base. The tray base may include at least one first post, a second post, and a projection or a groove configured to respectively secure the distal end portion, the proximal end portion, and a tether of the ureteral stent on the tray base.

16 Claims, 15 Drawing Sheets

(56) References Cited

U.S. PATENT DOCUMENTS

| | | | | |
|---|---|---|---|---|
| 5,947,284 | A * | 9/1999 | Foster | A61B 50/30 206/364 |
| 6,047,815 | A * | 4/2000 | Gerwin | A61B 17/06133 206/480 |
| 6,394,269 | B1 * | 5/2002 | Rudnick | A61B 17/06133 206/380 |
| 6,405,863 | B1 | 6/2002 | Dhindsa | |
| 6,533,116 | B1 * | 3/2003 | Riley | A61B 50/20 206/363 |
| 7,000,770 | B2 | 2/2006 | Clarke et al. | |
| 7,434,687 | B2 * | 10/2008 | Itou | A61M 25/002 206/370 |
| 8,241,319 | B2 | 8/2012 | Gilson et al. | |
| 8,672,881 | B2 * | 3/2014 | Nagamatsu | A61M 25/1002 604/97.02 |
| 2002/0049467 | A1 * | 4/2002 | Gilson | A61F 2/013 606/200 |
| 2003/0062281 | A1 * | 4/2003 | Giard, Jr. | A61B 5/150305 206/363 |
| 2004/0187438 | A1 | 9/2004 | Clarke et al. | |
| 2004/0243214 | A1 | 12/2004 | Farrell et al. | |
| 2005/0278012 | A1 | 12/2005 | Vonderwalde | |
| 2010/0140115 | A1 * | 6/2010 | Kirsch | A61B 17/06133 206/63.3 |
| 2011/0042244 | A1 * | 2/2011 | Kirsch | A61B 17/06133 53/485 |
| 2017/0056149 | A1 * | 3/2017 | Rajpara | A61F 2/0095 |
| 2018/0021542 | A1 * | 1/2018 | Terzibashian | A61B 50/30 206/363 |
| 2018/0250495 | A1 * | 9/2018 | McNabb | A61M 25/002 |

OTHER PUBLICATIONS

Two-piece tray delivers surgical stents, dated Feb. 29, 2004; https://www.packworld.com/article/package-type/thermoformed-packaging/two-piece-tray-delivers-surgical-stents, 8 pp.

International Preliminary Report on Patentability from corresponding International application No. PCT/US2019/068718, 9pp., dated Dec. 17, 2020.

* cited by examiner

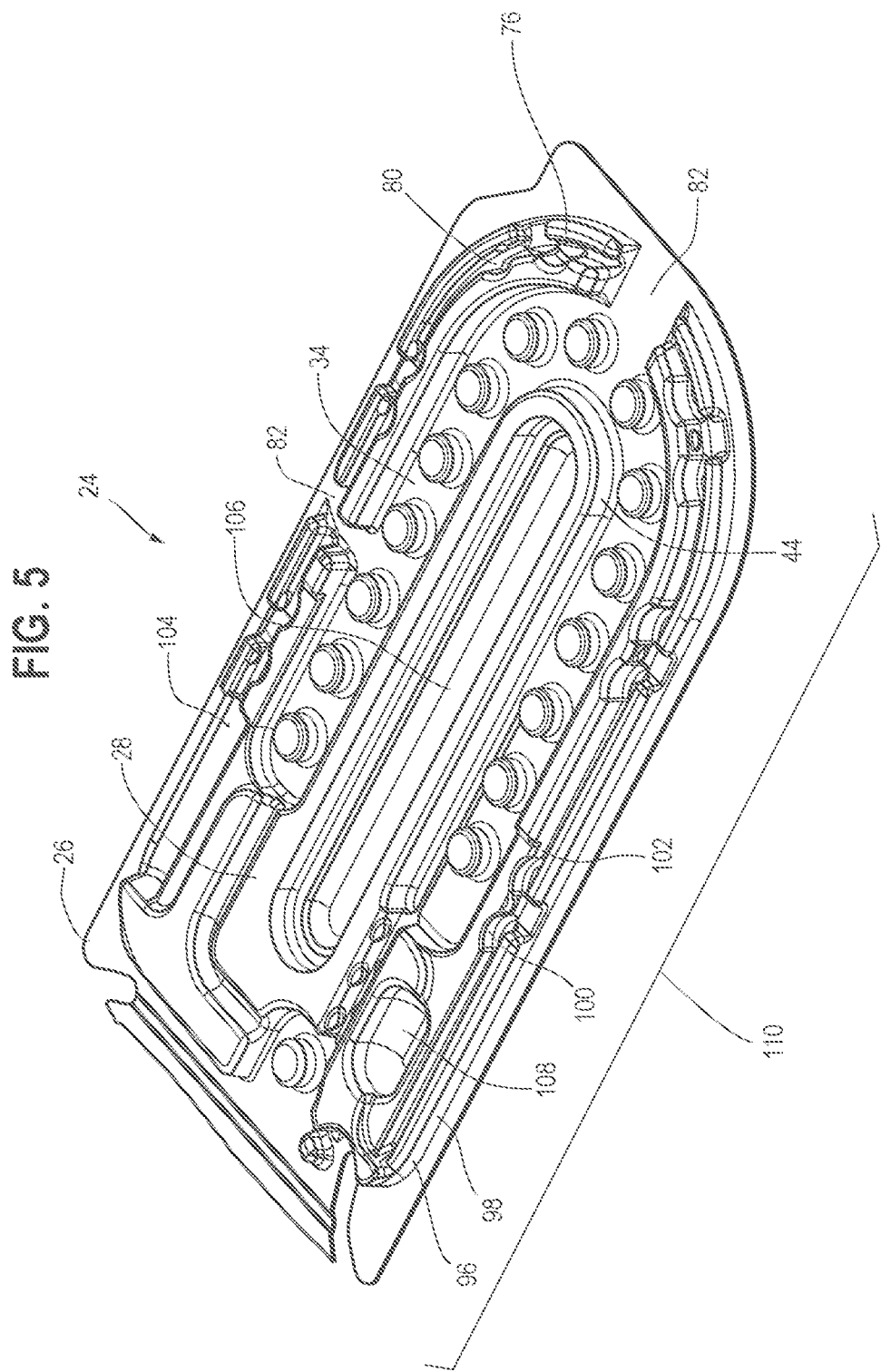

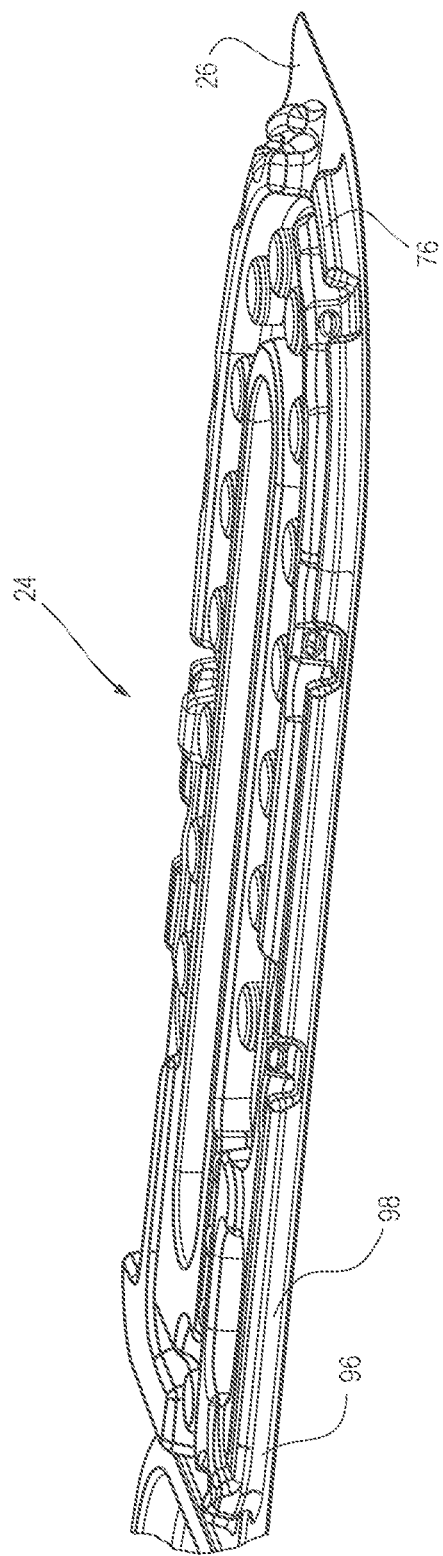

PACKAGING SYSTEM FOR URETERAL STENT

CROSS-REFERENCE TO RELATED APPLICATIONS

This patent application claims priority from U.S. Provisional Application No. 62/788,414, filed on Jan. 4, 2019, the entirety of which is hereby fully incorporated by reference herein.

BACKGROUND

Ureteral stents are in common use today. These stents are used during treatment of urological diseases that affect the urinary tract, including kidney and ureteral stone removal, strictures, tumors, and other ailments that can lead to hydronephrosis. Ureteral stents are placed to provide drainage through the ureter before or after a procedure and prevent the ureter from contracting and creating a blockage. A tether is placed on the proximal end of the ureteral stent and is used for repositioning or removal of the ureteral stent. Conventionally, ureteral stents are packaged in a pouch along with all the other components needed to place the stent (e.g., a positioner, a pigtail straightener). This may have one or more drawbacks, including the twisting or kinking of the stent, the entanglement of the stent and the other components, and the tether getting wrapped around the stent or the other components, which provide more opportunities for damage or loss of sterility and make it difficult or impossible for end users to prep the stent and components for procedural use.

DESCRIPTION OF THE DRAWINGS

The present disclosure can be better understood with reference to the following drawings and description. The components in the figures are not necessarily to scale, emphasis instead being placed upon illustrating the principles of the present disclosure. Moreover, in the figures, like-referenced numerals designate corresponding parts throughout the different views.

FIG. 5 is an illustration showing a perspective view of the tray base of FIG. 4 in accordance with certain aspects of the present disclosure.

FIG. 6 is an illustration showing another perspective view of the tray base of FIG. 4 in accordance with certain aspects of the present disclosure.

DETAILED DESCRIPTION

Figure 1:
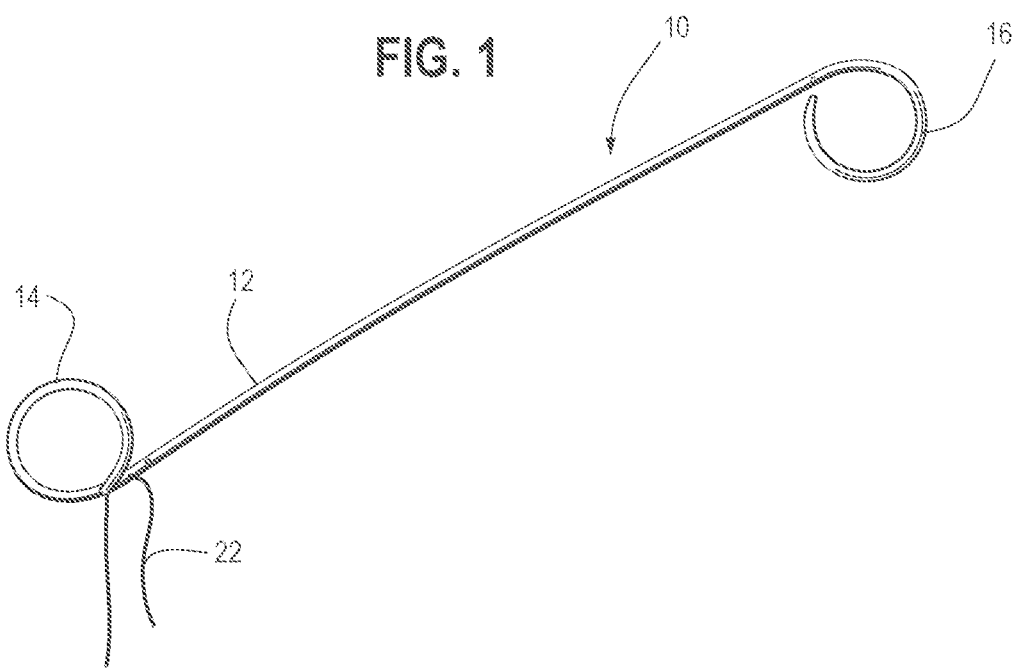
FIG. 1 is an illustration showing a perspective view of a ureteral stent including a tether in accordance with certain aspects of the present disclosure.

Various aspects are described below with reference to the drawings in which like elements generally are identified by like numerals. The relationship and functioning of the various elements of the aspects may better be understood by reference to the following detailed description. However, aspects are not limited to those illustrated in the drawings or explicitly described below. It also should be understood that the drawings are not necessarily to scale, and in certain instances details may have been omitted that are not necessary for an understanding of aspects disclosed herein, such as conventional material, construction, and assembly.

One general aspect of the present disclosure includes a packaging system for use with a ureteral stent having an elongated shaft extending between a proximal end portion and a distal end portion, including a tray base, where the tray base includes: a first extension disposed outwardly from a planar surface of the tray base and extending along at least a portion of a length of the tray base; at least one first post disposed outwardly from the planar surface of the tray base and adjacent to the first extension, where the at least one first post is configured to secure the distal end portion of the ureteral stent on the tray base; a second post disposed outwardly from the planar surface of the tray base and apart from the at least one first post by a first distance, where the second post is configured to secure the proximal end portion of the ureteral stent on the tray base; and a projection disposed outwardly from the planar surface of the tray base and adjacent to the second post, where the projection is configured to secure a tether coupled to the proximal end portion of the ureteral stent on the tray base.

Another general aspect of the present disclosure includes a packaging system for use with a ureteral stent having an elongated shaft extending between a proximal end portion and a distal end portion, including a tray base, where the tray base includes: at least one first post disposed outwardly from a planar surface of the tray base, where the at least one first post is configured to secure the distal end portion of the ureteral stent on the tray base; a second post disposed outwardly from the planar surface of the tray base and apart from the at least one first post by a first distance, where the second post is configured to secure the proximal end portion of the ureteral stent on the tray base; and a projection disposed outwardly from the planar surface of the tray base and adjacent to the second post, where the projection is configured to secure a tether coupled to the proximal end portion of the ureteral stent on the tray base.

Another general aspect of the present disclosure includes a packaging system for use with a ureteral stent having an elongated shaft extending between a proximal end portion and a distal end portion, including a tray base, where the tray base includes: at least one first post disposed outwardly from a planar surface of the tray base, where the at least one first post is configured to secure the distal end portion of the ureteral stent on the tray base; a second post disposed outwardly from the planar surface of the tray base and apart from the at least one first post by a first distance, where the second post is configured to secure the proximal end portion of the ureteral stent on the tray base; and an extension disposed outwardly from the planar surface of the tray base, where the extension includes a groove extending along at least a portion of an outer edge of the extension to releasably receive a tether of the ureteral stent therein.

Figure 2:
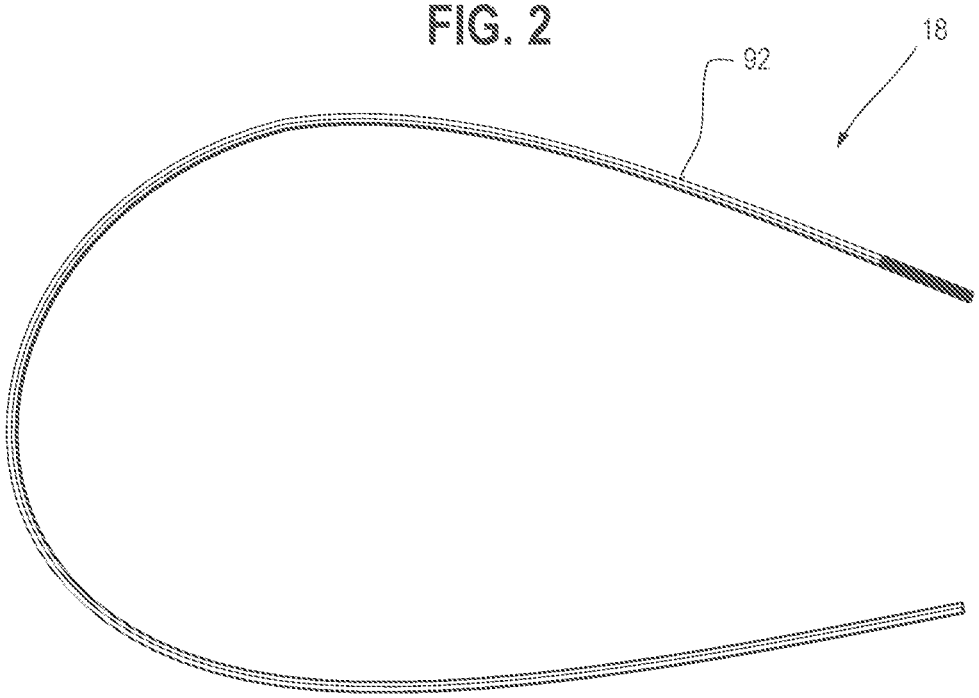
FIG. 2 is an illustration showing a perspective view of a positioner in accordance with certain aspects of the present disclosure.
Figure 3:
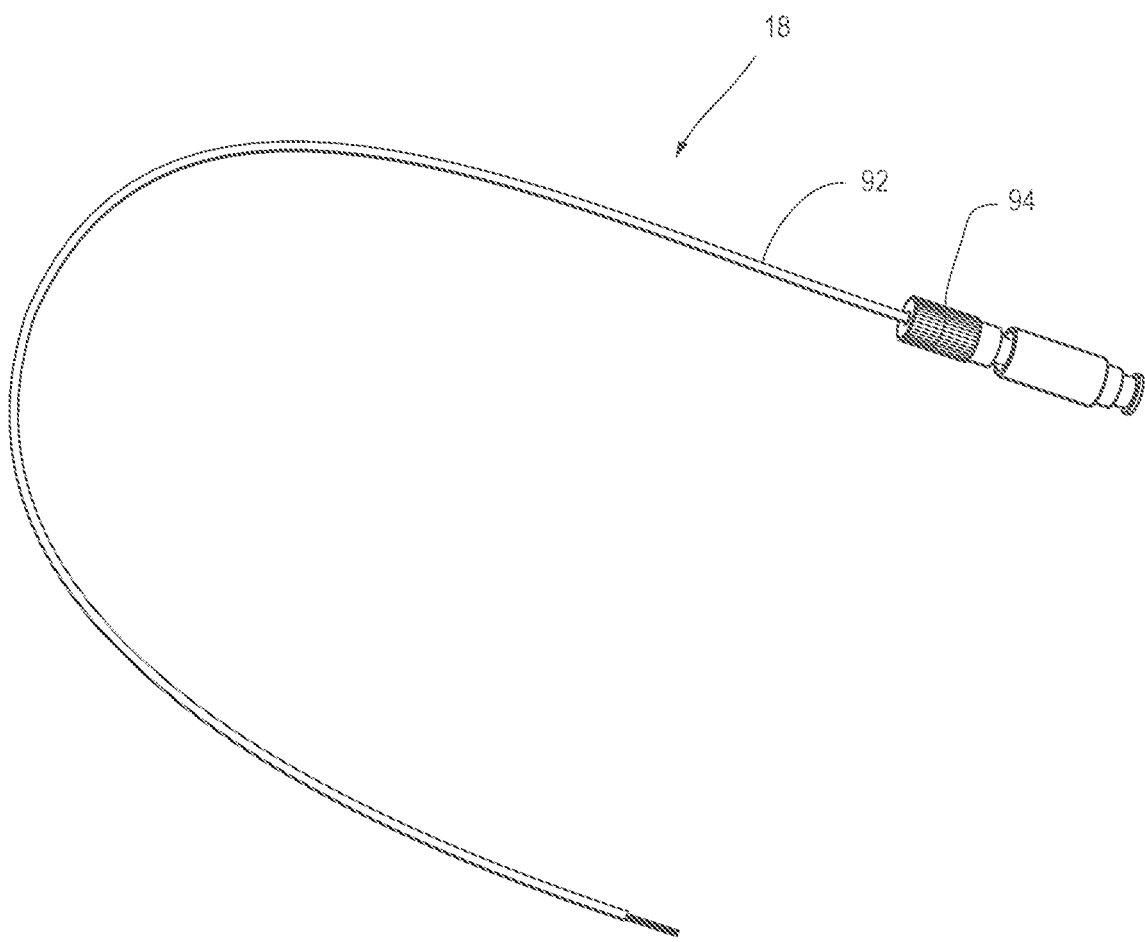
FIG. 3 is an illustration showing a perspective view of a positioner including an actuator in accordance with certain aspects of the present disclosure.

Referring to FIG. 1, a ureteral stent 10 including an elongated shaft extending between a proximal end portion 14 and a distal end portion 16 is shown. While a ureteral stent 10 is specifically described herein, the packaging system 24 may be successfully implemented for stents for other clinical uses, or for other elongate medical devices. For the sake of brevity, a packaging system for ureteral stents is described in detail herein, and one of ordinary skill in the art, with a thorough review of the subject specification and figures, would readily comprehend how the packaging system may be implemented for stents for other clinical uses or other medical devices without undue experimentation. In some embodiments, as shown in FIG. 1, the elongated shaft 12 of a ureteral stent 10 may have a relatively straight configuration and the proximal and distal end portions 14 and 16 may have a pigtail configuration. In use, the ureteral stent 10 may be positioned in the ureter over a wire guide and with the use of a positioner 18 including an elongated tubular body 92 (FIG. 2) or including the elongated tubular body 92 with an actuator 94 coupled to the elongated tubular body 92 (FIG. 3). A tether 22 may be coupled to the proximal end portion 14 of the ureteral stent 10 or a portion of the shaft 12 proximate to the proximal end portion 14. The ureteral stent 10 and the positioner 18 may be sufficiently flexible to allow them to be curved for packaging, but be sufficiently elastic or resilient so as to resume their original shapes for the implantation procedure.

Referring to FIGS. 4-12, a packaging system 24 for use with the ureteral stent 10 and the positioner 18 is shown. The packaging system 24 may include a tray base 26 configured to releasably receive the ureteral stent 10 and the positioner 18 therein. The tray base 26 may be formed from any suitable material for releasably receiving the ureteral stent 10 and the positioner 18. For example, the tray base 26 may be formed from plastic materials, such as polyethylene, polycarbonate, polyvinyl chloride, polyurethane, and other suitable materials. The tray base 26 may be made through a plastic thermoforming process. In some embodiments, the tray base 26 may be of generally rectangular configuration with angled or chamfered corners, as shown in FIGS. 8-12. It will be appreciated that various configurations of the tray base 26 may be provided as needed and/or desired without departing from the scope of the present invention.

Figure 7:
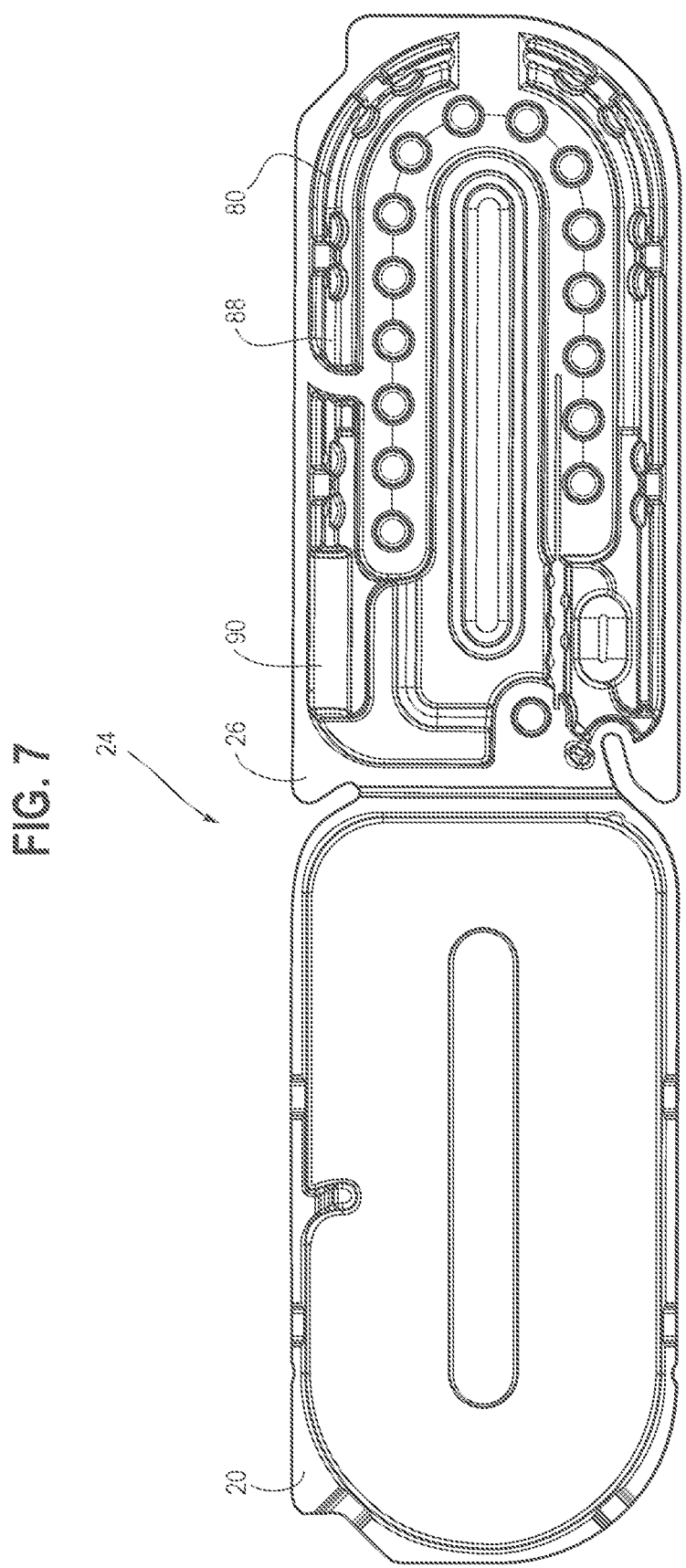
FIG. 7 is an illustration showing a top view of a packaging system including a tray base and a tray cover in accordance with certain aspects of the present disclosure.
Figure 9:
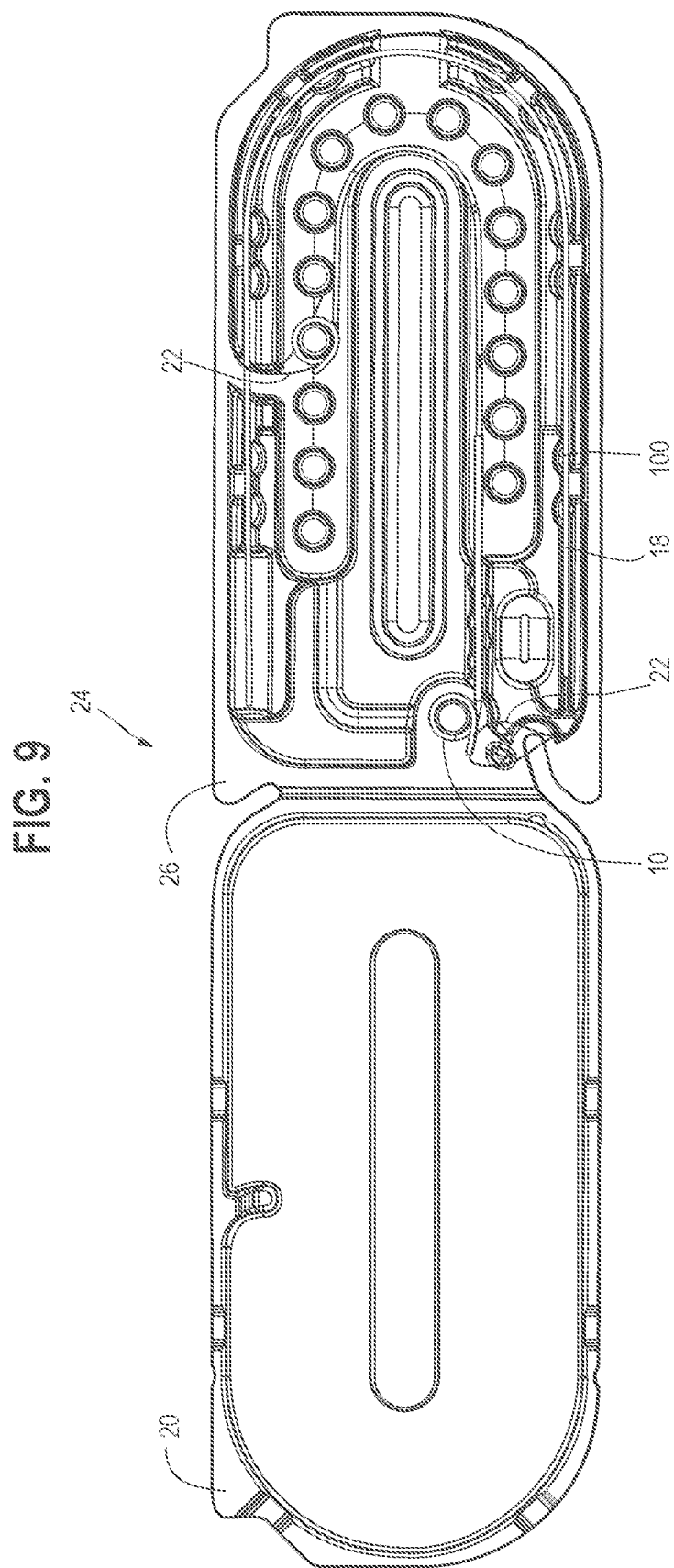
FIG. 9 is an illustration showing a perspective view of a packaging system including a try base and a tray cover, where the tray base contains a ureteral stent and the positioner of FIG. 2 in accordance with certain aspects of the present disclosure.

In some embodiments, as shown in FIGS. 7 and 9, the packaging system 24 may also include a tray cover 20. The tray cover 20 may be configured to releasably fit onto the tray base 26 such that the ureteral stent 10 and positioner 18 may be disposed between the tray base 26 and the tray cover 20. In some embodiments, the tray cover 20 may be a snap fit with the tray base 26. In some embodiments, the tray cover 20 may be connected to the tray base 26 with a hinge (FIG. 7) such that the tray cover 20 is fixed to the tray base, while in other embodiments, (FIG. 13, FIG. 14) an alternate tray cover 120 may be provided that is a separate component from the tray base 26. This embodiment allows the tray cover 120 be withdrawn from the tray base while minimizing the space that the packaging system 24 takes up when opened. In some embodiments, the packaging system 24 may also include a sealable pouch (not shown). The covered tray with the ureteral stent 10 and the positioner 18 may be placed within the sealable pouch for packaging. It will be appreciated that any suitable material and configuration for packaging, sterilization, and storage may be used with the tray cover and the pouch.

The tray base 26 may include a first extension 28 disposed outwardly from a planar surface 30 of the tray base 26. The first extension 28 may extend along at least a portion of a length of the tray base 26. In some embodiments, as shown, the first extension 28 may have a U-shaped configuration. It will be appreciated that the configuration of the first extension 28 may be varied as desired and/or needed to accommodate varying design needs of the tray base 26. For example, the first extension 28 may be generally rectangular, square or circular, or any suitable shape to allow at least a portion of the elongated shaft 12 of the ureteral stent 10 to extend around an outer edge 44 of the first extension 28. The tray base 26 may also include at least one first post 32, and as shown, a plurality of first posts 32, configured to releasably secure the distal end portion 16 of the ureteral stent 10 thereto. The tray base 26 may also include a second post 40 disposed outwardly from the planar surface 30 of the tray base 26 and apart from the at least one first post 32 by a first distance 42. The second post 40 may be configured to releasably secure the proximal end portion 14 of the ureteral stent 10 thereto. In some embodiments, as shown in FIGS. 5 and 8-12, the first and second posts 32 and 40 both may be provided in a cylindrical configuration having a circular cross section with a diameter that is similar to or slightly smaller than the respective distal and proximal end portions 16 and 14 when the distal and proximal end portions 16 and 14 are disposed in their nominal pigtail shaped orientation (e.g., the pigtail shaped distal and proximal end portions 16 and 14 may have an inner diameter ranging from 0.3 inch to 0.7 inch). For example, the inner diameter of the first and second posts 32 and 40 may range from 0.2 inch to 0.7 inch. This allows the pigtail-shaped distal and proximal end portions 16 and 14 of the ureteral stent 10 to be placed around the respective first and second posts 32 and 40, such that the distal and proximal end portions 16 and 14 of the ureteral stent 10 can be secured to the tray base 26 while retaining their respective pigtail shapes. Additional configurations for the cross-sectional shape of the first and second posts 32 and 40 are possible including, but not limited to, oval, square, rectangular, triangular and combinations thereof. It will be appreciated that the configuration (e.g., shape and dimension) of the first post 32 and the second post 40 may be varied as needed and/or desired to accommodate the configuration of the distal and proximal end portions 16 and 14 of the ureteral stent 10 respectively. This configuration provides the ability to stabilize the ureteral stent 10 during transport, minimize damage to the ureteral stent 10, and prevent deformation of the proximal and distal end portions 14 and 16 of the ureteral stent 10.

Figure 10:
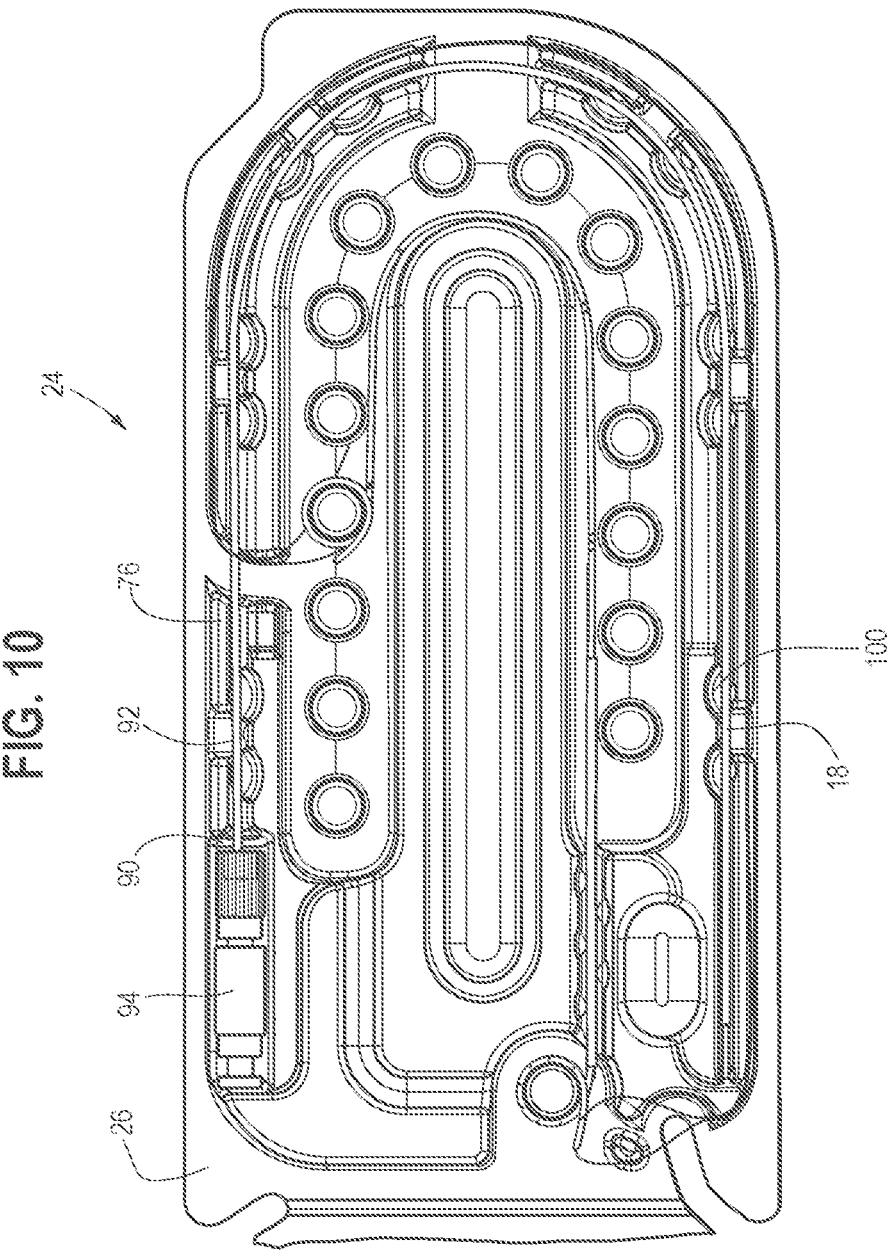
FIG. 10 is an illustration showing a perspective view of the tray base of FIG. 4 with a ureteral stent and the positioner of FIG. 3 loaded thereon in accordance with certain aspects of the present disclosure.
Figure 11:
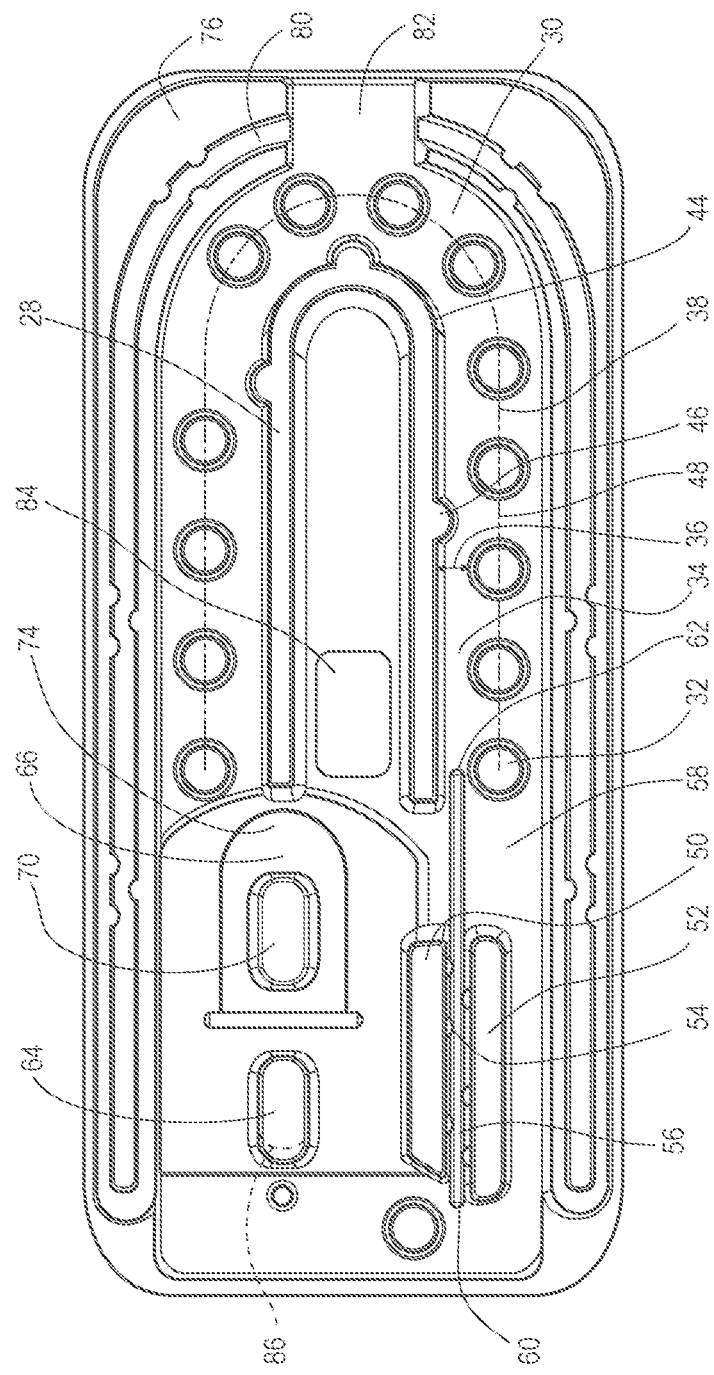
FIG. 11 is an illustration showing a perspective view of a tray base including a flap and a projection in accordance with certain aspects of the present disclosure.
Figure 12:
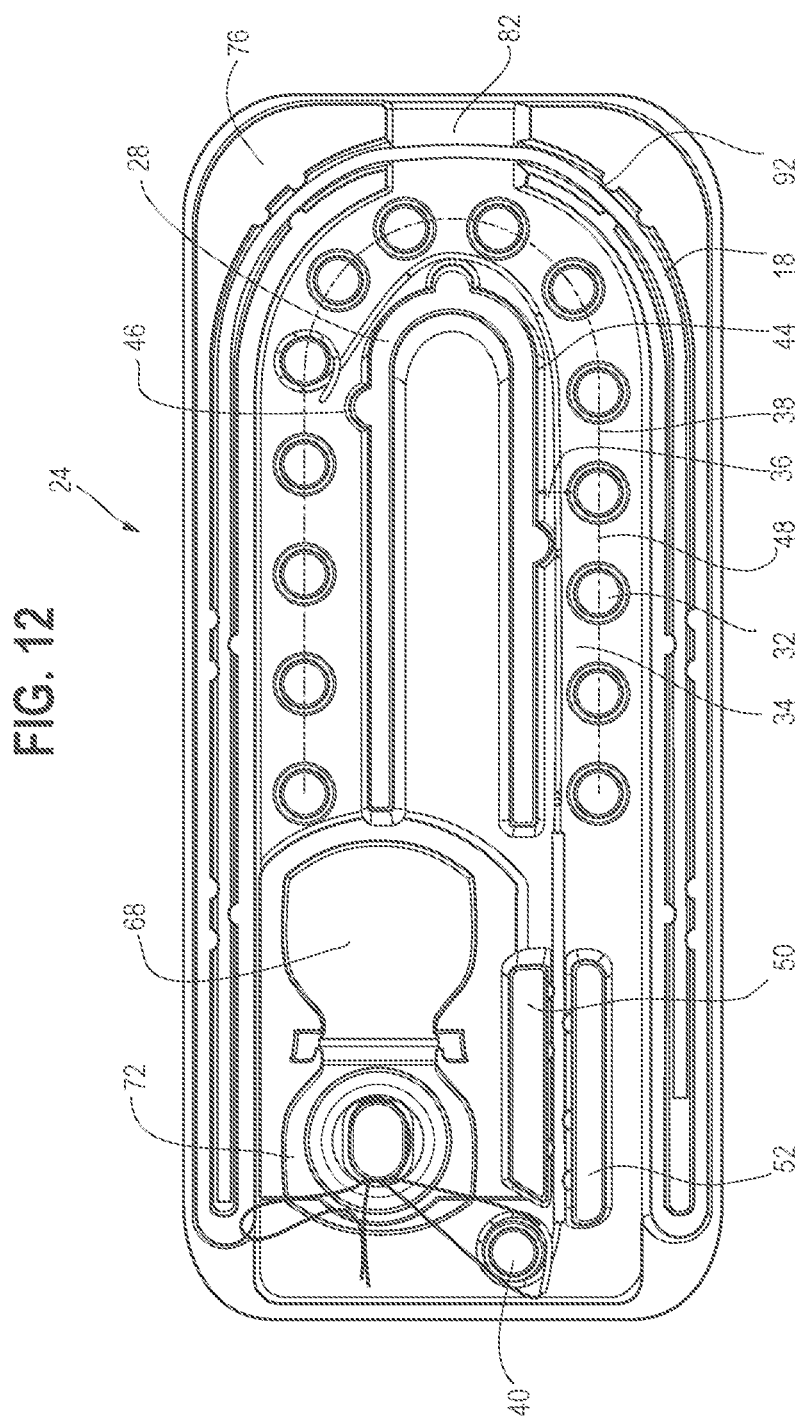
FIG. 12 is an illustration showing a perspective view of a tray base including a flap and a projection, having a ureteral stent and the positioner of FIG. 2 loaded thereon in accordance with certain aspects of the present disclosure.

The plurality of first posts 32 may be disposed outwardly from the planar surface 30 of the tray base 26 and adjacent to the first extension 28. In some embodiments, the plurality of first posts 32 may be disposed along a line 38 that extends parallel to at least a portion of the first extension 28. For example, as shown in FIG. 11, the plurality of first posts 32 are disposed along a U-shaped line 38 extending substantially parallel to the U-shaped first extension 28 while being spaced apart from the first extension 28 by a second distance 36. Spaces upon the planar surface 30 of the tray base 26 between the first extension 28 and the at least one first post 32 (e.g., the plurality of first posts 32, as shown) collectively define a first valley 34 such that at least a portion of the elongated shaft 12 of the ureteral stent 10 may be releasably received therein (e.g., as shown in FIG. 12). For example, as shown in FIGS. 8-12, at least a portion of the elongated shaft 12 of the ureteral stent 10 may be releasably snapped into the first valley 34 and extends around the outer edge 44 of the first extension 28. It will be appreciated that the configuration of the first extension 28, the plurality of first posts 32, and the first valley 34 may be configured to hold the ureteral stent 10 within the first valley 34 in a desired configuration (e.g., the U-shaped configuration shown in FIGS. 8-12), such that a smaller overall dimension of the tray base 26 may be achieved. In some embodiments, the first extension 28 may be provided with at least one tab 46, and as shown in FIG. 11, a plurality of tabs 46, extending from the outer edge 44 of the first extension 28 to the first valley 34 to facilitate holding the ureteral stent 10 received within the first valley 34 in place. In some embodiments, the at least one tab 46 may extend from the outer edge 44 of the first extension 28 to a void 48 located on the line 38 between two adjacent first posts 32. It will be appreciated that the configuration, number, spacing, and arrangement of tabs 46 may be varied as needed and/or desired. In some embodiments, the first extension 28, the at least one first post 32, and the second distance 36 may be configured such that the first valley 34 has a diameter similar to or slightly greater than an outer diameter of the elongated shaft 12 of the ureteral stent 10 (e.g., ranging from 0.4 inch to 0.5 inch). The term "about" is specifically defined herein to include the specific value referenced as well as a dimension that is within 5% of the dimension both above and below the dimension. This will minimize radial twisting movement of the elongated shaft 12 of the ureteral stent 10 within the first valley 34. It will be appreciated that the configuration (e.g., the height) of the first extension 28 and the at least one first post 32, and the length of the second distance 36 may be varied as needed and/or desired to accommodate the configuration (e.g., varying outer diameters) of ureteral stents 10.

Figure 4:
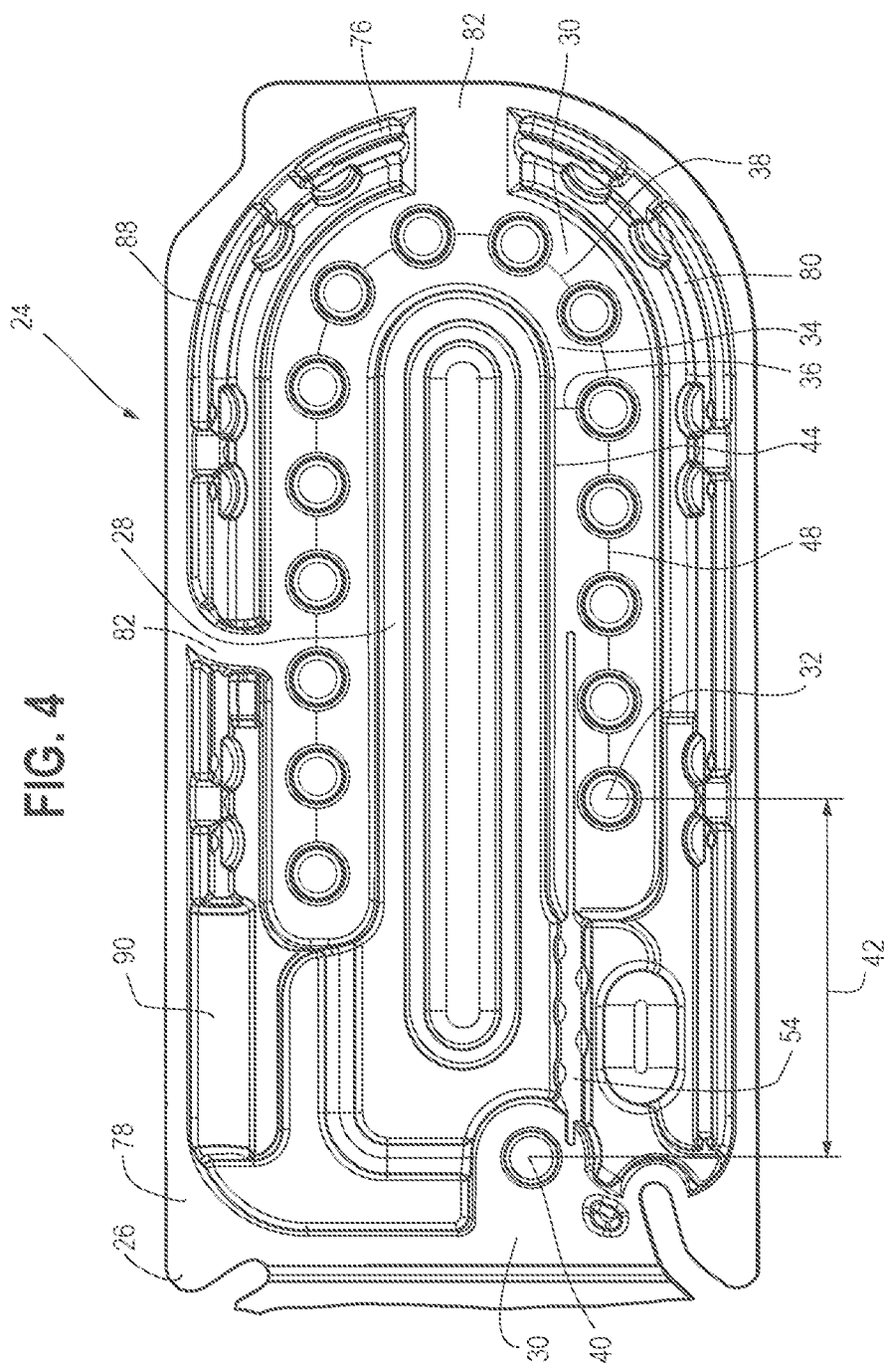
FIG. 4 is an illustration showing a top view of a tray base in accordance with certain aspects of the present disclosure.

The plurality of first posts 32 may be spaced apart along the line 38. Each of the plurality of first posts 32 may be placed at any desired location along the length of the line 38. For example, as shown in FIG. 4, some of the plurality of first posts 32 may be spaced at substantially uniform distances while some of the plurality of first posts 32 may be spaced at different distances. The first distance 42 between the at least one first post 32 and the second post 40 may be varied to accommodate varying lengths of the ureteral stent 10. For example, the first distance 42 may range from about 4 cm to about 40 cm. In some embodiments, when the tray base 26 include a plurality of first posts 32 (e.g., as shown in FIG. 4), the first distance 42 between each first post 32 and the second post 40 may be configured such that the proximal end portions 14 and the distal end portions 16 of ureteral stents 10 with different lengths may be releasably secured to the second post 40 and differing ones of the first posts 32. The number of the first posts 32 disposed on the tray base 26 may be varied as desired and/or needed, for example, may be any number from 1 to 20. In some embodiments, 15 first posts 32 are provided on the tray base 26. The greater the number of the first posts 32 disposed on the tray base 26, the greater the number of ureteral stents 10 with varying lengths may be accommodated. It will be appreciated that the configuration (e.g., the overall length) of the first extension 28, the first distance 42, and the number, spacing, and arrangement of the first posts 32 along the line 38 may be varied as needed and/or desired to accommodate varying lengths of ureteral stents 10. Although many suitable configurations and arrangements are conceivable, the configurations and arrangements must be such that the first distance 42 between the second post 40 and at least one of the plurality of first posts 32 allows the proximal and distal end portions of a ureteral stent 10 to be releasably secured to the second post 40 and the at least one of the plurality of first posts 32 respectively. Instead of forming tray bases 26 with different configurations, by forming a single tray base 26 with a plurality of spaced-apart first posts 32 to accommodate ureteral stents 10 with varying lengths, waste may be decreased, recyclability may be simplified, manufacturing efficiency may be increased, and manufacturing costs may be reduced. Spacing each of the first posts 32 and the second post 40 at a distance corresponding to a particular length of a ureteral stent 10 will minimize axial twisting movement of the elongated shaft 12 of the ureteral stent 10 and thereby reducing potential damage to the ureteral stent 10 during transport.

The tray base 26 may include a third extension 50 and a fourth extension 52 disposed outwardly from the planar surface 30 of the tray base 26 and adjacent to the second post 40. The third and fourth extensions 50 and 52 may extend along at least a portion of the length of the tray base 26. In some embodiments, as shown in FIG. 11, the third and fourth extensions 50 and 52 may extend substantially parallel to each other. Spaces upon the planar surface 30 of the tray base 26 between the third and fourth extensions 50 and 52 may define a second valley 54 such that at least a portion of the elongated shaft 12 of the ureteral stent 10 may be releasably received therein (e.g., as shown in FIG. 12). In some embodiments, the third and fourth extensions 50 and 52 may be configured such that the second valley 54 is aligned collinearly with at least a portion of the first valley 34. As such, the ureteral stent 10 may extend through the second valley 54 and the first valley 34 with the proximal end portion 14 and the distal end portion 16 being secured to the second post 40 and one of the first posts 32 respectively. The third and fourth extensions 50 and 52 may provide an additional holding power to hold the ureteral stent 10 in place. In some embodiments, as shown in FIG. 11, spaces on the planar surface 30 of the tray base 26 between the first valley 34 and the second valley 54 may define a first notch 58 configured for easy removal of the ureteral stent 10 received within the first and second valleys 34 and 54.

The tray base 26 may include a first recess 56 configured to releasably receive at least a portion of the elongated shaft 12 of the ureteral stent 10, such that an extra holding power may be provided to hold the ureteral stent 10 in place. In some embodiments, the first recess 56 may extend from a first place 60 proximate to the second post 40 to a second position 62 proximate to the at least one first post 32 (e.g., as shown in FIG. 11). It will be appreciated that the configuration and length of the first recess 56 may be varied as needed and/or desired to accommodate the configuration and length of the ureteral stent 10 received therein without departing from the scope of the present invention. For example, as shown in FIG. 11, the first recess 56 may extend through the second valley 54, past the first notch 58, and into at least a portion of the first valley 34. As such, the elongated shaft 12 of the ureteral stent 10 may be snapped into the first and second valleys 34 and 54 and then into the first recess 56.

In some embodiments, as shown in FIGS. 11-12, the tray base 26 may include a projection 64 disposed outwardly from the planar surface 30 of the tray base 26 and adjacent to the second post 40. The projection 64 may be configured to secure thereto the tether 22 coupled to the proximal end portion 14 of the ureteral stent 10. The projection 64 may be positioned such that the tether 22 may be wrapped around the projection 64 while the proximal end portion 14 of the ureteral stent 10 is placed around the second post 40. In some embodiments, the projection 64 may be provided in a cylindrical configuration having a circular cross section (e.g., as shown in FIG. 11). Additional configurations for the cross-sectional shape of the projection 64 are possible including, but not limited to, oval, square, rectangular, triangular and combinations thereof. It will be appreciated that the configuration of the projection 64 may be varied as needed and/or desired without departing from the scope of the present invention. In some embodiments, the projection 64 may be provided with an under-cut 86 at the base of the projection 64 so as to provide the ability to efficiently wrap and secure the tether 22 around the projection 64. The under-cut 86 is defined by a portion of the projection 64 below a top surface of the projection 64 that has a smaller circumference or cross-section than the top surface. In some embodiments, the projection 64 may be removable from the tray base 26, such that a user may wrap the tether 22 around the projection 64 first and then snap the projection 64 to the tray base 26.

The tray base 26 may include a flap 66 hingedly mounted at a desired location adjacent to the projection 64. The flap 66 may include a first groove 70 configured to be a snap fit with the projection 64. In some embodiments, as shown in FIG. 11, the first groove 70 may be provided in a shape similar to or substantially the same as the projection 64 while having a dimension slightly larger than the projection 64. The flap 66 may be hingedly movable between a third position 72 (e.g., as shown in FIG. 12) and a fourth position 74 (e.g., as shown in FIG. 11). When the flap 66 is moved to the fourth position 74, the flap 66 closes an aperture 68 of the tray base 26 where the flap 66 is held in place by a snap fit. When the flap 66 is moved to the third position 72, the flap 66 may be secured to the projection 64 by a snap fit with the projection 64 being received within the first groove 70. This configuration allows the tether 22 wrapped around the projection 64 to be releasably secured thereto by the snap-fit closure of the flap 66 and the projection 64, without the need of securely tying together the tether 22 and the projection 64. As such, the tether 22 may be easily released by lifting the flap 66. This configuration provides various advantages, such as quick, easy, and simple securement and removal of the tether 22, and reducing possibility of damaging the tether 22. The projection 64 and the flap 66 may also prevent the tether 22 from getting tangled around the ureteral stent 10 and/or other components packed together, such that damage to the tether 22 may be reduced, and the process of prepping the ureteral stent 10 before use may be simplified.

The tray base 26 may also include a second extension 76 disposed outwardly from the planar surface 30 of the tray base 26. In some embodiments, the second extension 76 may extend along at least a portion of a peripheral portion 78 of the tray base 26. For example, as shown in FIG. 11, the second extension 76 may have a generally U shape and may extend along three edges of the tray base 26. In some embodiments, the at least one first post 32, and as shown, the plurality of first posts 32 may be disposed between at least a portion of the first extension 28 and at least a portion of the second extension 76. The second extension 76 may include a second recess 80 configured to releasably receive (e.g., by a snap fit) a positioner 18 therein. It will be appreciated that the configuration of the second extension 76 and the second recess 80 may be varied as needed and/or desired to accommodate positioners 18 with varying configurations. For example, the length of the second recess 80 may vary depending on the length of the positioner 18. In some embodiments, as shown in FIG. 12, the positioner 18 may extend substantially the entire length of the second recess 80, which will minimize axial twisting movement of the positioner 18 within the second recess 80. The dimension of the second recess 80 may vary depending on the outer diameter of the positioner 18 so as to minimize radial twisting movement of the positioner 18 within the second recess 80. In some embodiments, the dimension of the second recess 80 may vary along the length of the second recess 80 to accommodate different outer diameters along the length of the positioner 18. For example, as shown in FIGS. 4, 7 and 10, a first portion 88 of the second recess 80 is configured to accommodate the elongated tubular body 92 of the positioner 18 and a second portion 90 of the second recess 80 is configured to accommodate the actuator 94 of the positioner 18. In some embodiments, as shown in FIGS. 5 and 8-10, the second recess 80 may include at least one second groove 100 disposed in the inner edge 102 of the second recess 80 for easy removal of the positioner 18 disposed therein.

Figure 8:
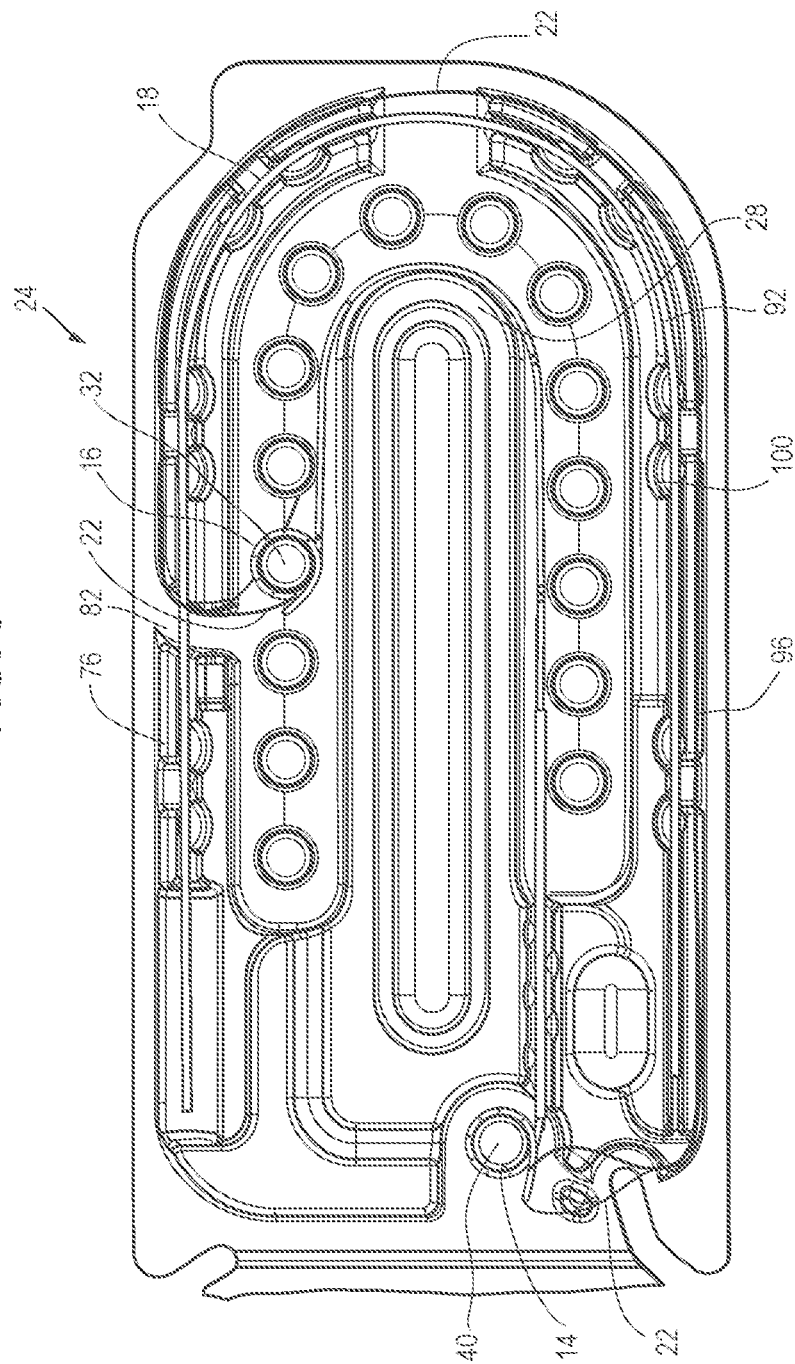
FIG. 8 is an illustration showing a perspective view of a tray base with a ureteral stent and the positioner of FIG. 2 loaded thereon in accordance with certain aspects of the present disclosure.

In some embodiments, as shown in FIG. 5, the second extension 76 may include at least one second notch 82 configured for easy removal of the positioner 18 received within the second recess 80 and/or for providing a passageway to allow the tether 22 of the ureteral stent 10 to extend from an outer edge 96 of the second extension 76 into the first valley 34. As shown in FIGS. 5-6, the outer edge 96 of the second extension 76 may include a third groove 98 extending along at least a portion of the outer edge 96 of the second extension 76 to releasably receive at least a portion of the tether 22. In use, as shown in FIGS. 8-10, when the proximal end portion 14 of the ureteral stent 10 is placed around the second post 40, the tether 22 coupled to the proximal end portion 14 may extend around the outer edge 96 of the second extension 76 within the third groove 98, and extend into the first valley 34 through a second notch 82 of the second extension 76, and then is wrapped around a first post 32 which the distal end portion 16 of the ureteral stent 10 is to be placed around.

This configuration allows the tether 22 wrapped around the first post 32 to be releasably secured thereto by the distal end portion 16 of the ureteral stent 10 without the need of securely tying together the tether 22 and the first post 32. At the same time, as shown in FIG. 8, by placing the positioner 18 within the second recess 80 in the second extension 76 and over the portion of the tether 22 that extends through the second notch 82, the tether 22 is further secured to the tray base 26 by the positioner 18. As such, the tether 22 may be easily released by lifting the distal end portion 16 of the ureteral stent 10 and the positioner 18. This configuration provides various advantages, such as quick, easy, and simple securement and removal of the tether 22 and preventing the tether 22 from getting tangled around the ureteral stent 10 and/or other components packed together, such that damage to the tether 22 may be reduced, and the process of prepping the ureteral stent 10 before use may be simplified.

Figure 5A:
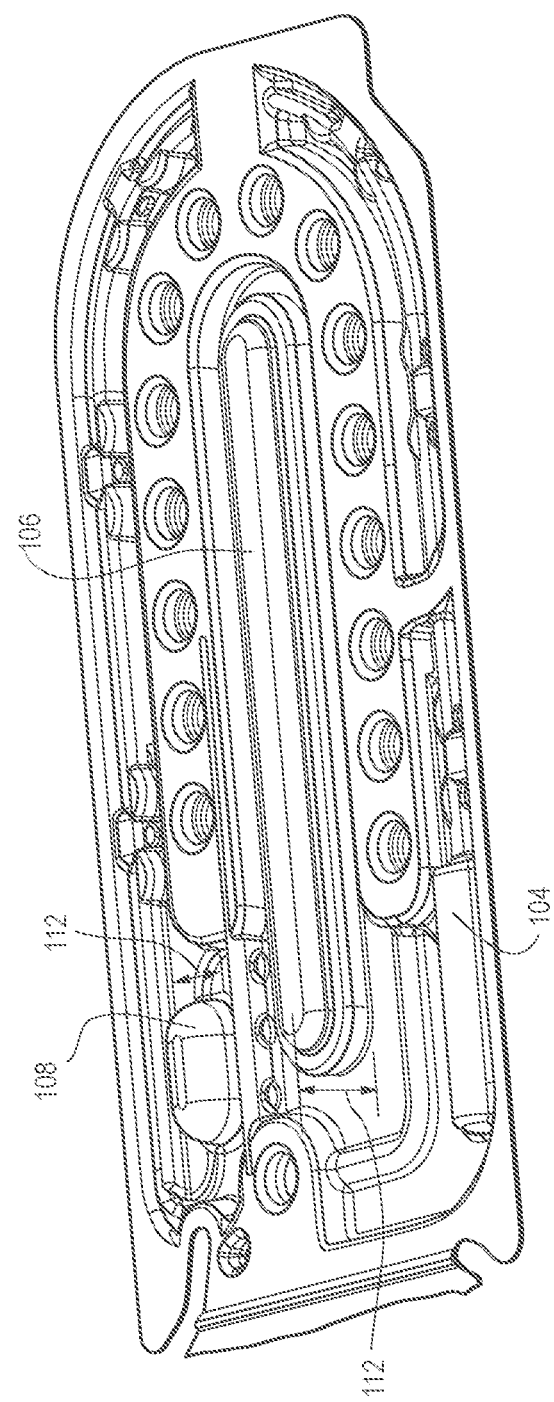
FIG. 5A is an illustration showing a bottom perspective view of the tray base of FIG. 4 in accordance with certain aspects of the present disclosure.

In some embodiments, as shown in FIGS. 5 and 5A, the tray base 26 may include a plurality of recessed cavities 104, 106 and 108. In some embodiments, the recessed cavities 104, 106 and 108 may have a same depth 112 such that the tray base may be laid horizontally and securely on a support 110 (e.g., a table or a cart). It will be appreciated that the number, configurations, orientations, lengths, depths, and spacing of the recessed cavities may be varied as desired and/or needed as long as the tray base 26 may be positioned as desired and/or needed.

In some embodiments, the tray base 26 may include one or more slots 84, which may be used for grabbing and holding onto the tray base 26 for ergonomic reasons. The slots 84 may be provided at convenient locations within the tray base 26, and are normally sized big enough to allow a user's fingers to engage the slots 84 (as shown in FIG. 11).

In use, a user may place the positioner 18 onto the tray base 26 such that the positioner 18 at least partially rests within the second recess 80. The user may place the ureteral stent 10 onto the tray base so that the proximal end portion 14 of the ureteral stent 10 is placed around the second post 40, the elongated shaft 12 of the ureteral stent 10 at least partially rests within and extend along at least a portion of the first and second valleys 34 and 54, and the distal end portion 16 of the ureteral stent 10 is placed around a first post 32. Then, the tether 22 coupled to the proximal end portion 14 of the ureteral stent 10 may be wrapped around the projection 64. The flap 66 may then be folded over and pressed down on top of the tether 22, such that the tether 22 is secured by a snap-fit connection of the flap 66 and the projection 64. In some embodiments, the user may place the tether 22 within the third groove 98 along the outer edge 96 of the second extension 76 first, wrap the tether 22 around a first post 32, and then place the distal end portion 16 of the ureteral stent 10 around the first post 32 that the tether 22 is wrapped around, and place the positioner 18 within the second recess 80 over the tether 22, such that the tether 22 is secured to the tray base 26 by the positioner 18 and the distal end portion 16 of the ureteral stent 10.

The tray base 26 may provide security to the components loaded thereon to prevent damage during transport. Separate snap-fit locations in the tray base 26 for each component loaded thereon (e.g., the positioner 18, the elongated shaft 12, the proximal end portion 14, the distal end portion 16, and the tether 22) provide an organized display to prevent entanglement of the components. In some embodiments, the tray cover may then be snapped in place covering the tray base 26 and the ureteral stent 10 and positioner 18 loaded thereon. The tray base 26 or the covered tray base may then be packaged into the pouch for sterilization and storage. The pouch is then sealed and sterilized in a conventional manner. Any type of sterilization procedure known to one of skill in the art for sterilizing medical devices may be used. The sterilized tray base 26 and the ureteral stent 10 and positioner 18 loaded thereon may be stored in the pouch until use in a medical procedure.

Turning now to FIGS. 13-16, further embodiments are provided that modify the embodiments discussed above. In the event that structure depicted in these figures is not discussed specifically herein, the structure in these embodiments is consistent with the structure discussed above. As discussed above, in some embodiments, an alternate tray cover 120 may be provided that is a separate component from the tray base 26. This embodiment allows the tray cover 20 be withdrawn from the tray base while minimizing the space that the packaging system 24 takes up when opened.

Figure 13:
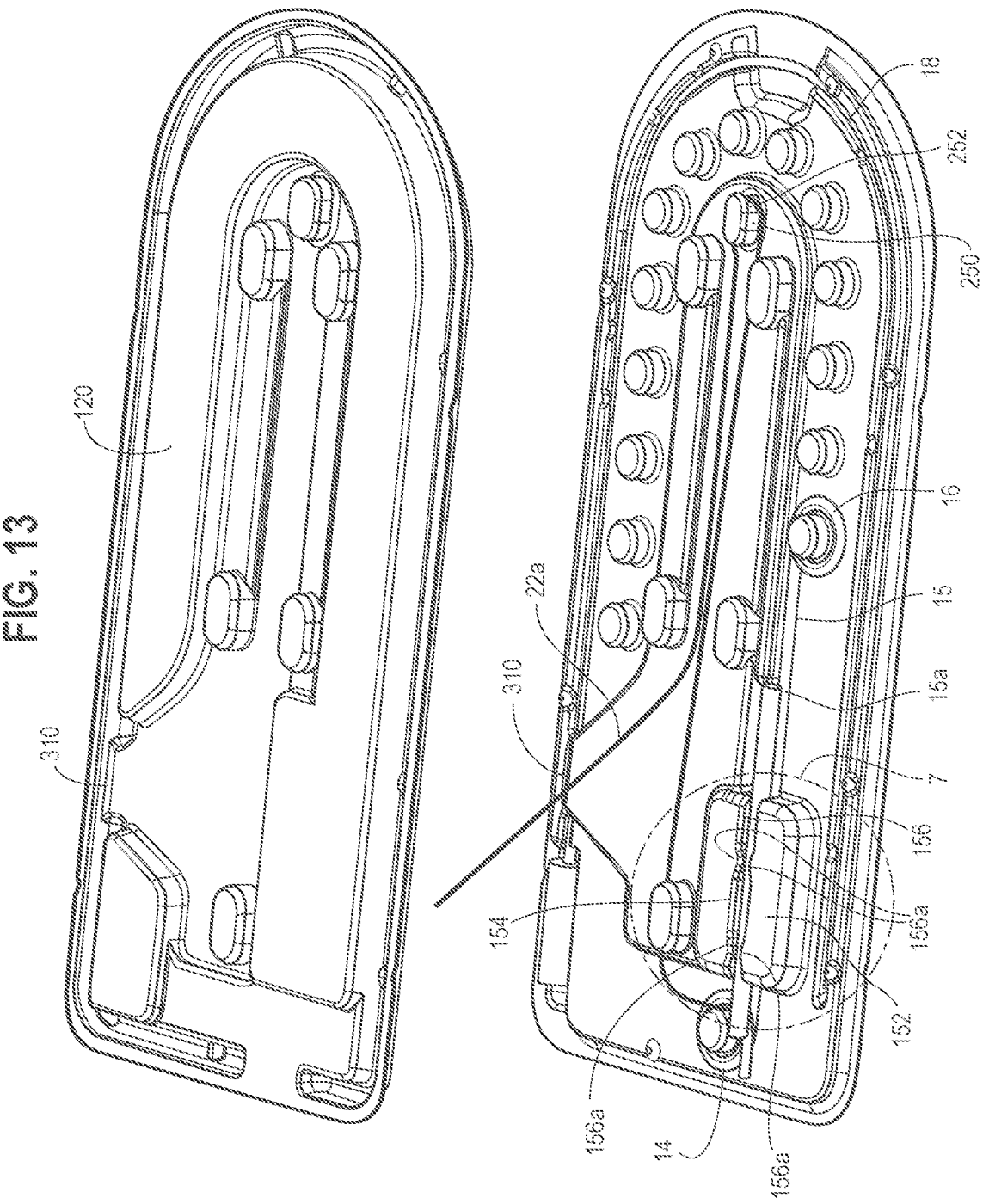
FIG. 13 is an illustration showing a perspective view of another embodiment of a packaging system including a tray base and a tray cover in accordance with certain aspects of the present disclosure.

In the embodiment depicted in FIGS. 13-16, the tray 26 may include a projection 250 that is positioned to receive a portion of the tether 22 that extends from the proximal end 16 of the device. The projection 250 may be positioned proximate to several of the first posts 32 and in some embodiments at or proximate to a center point of the collective first posts 32 that are arranged along a curve, as designated by W, with the position of the centerpoint designated schematically at point X. As depicted in FIG. 13, in this embodiment, the tray 26 may include a raised by first extension 28a, but which is at a height that is less than the height of the first posts 32, and in some embodiments, the height of the projection 250 being the same height as the height of the first posts 32. The projection 250 may include an under-cut 252 that receives the tether 22 and aligns the tether with respect to the projection 250 for ease of assembly. In some embodiments, the under-cut 252 may only extend around about one half of the circumference of the projection 250, such as for embodiments where the tether is not completely wrapped around the circumference of the projection 250 (FIG. 16, although the tether 22 not shown disposed within the under-cut 252 in this figure), while in other embodiments, the under-cut 252 may wrap around the entire circumference of the projection 250 to align the tether when it is configured to wrap completely around the projection 250 one or more times.

Figure 14:
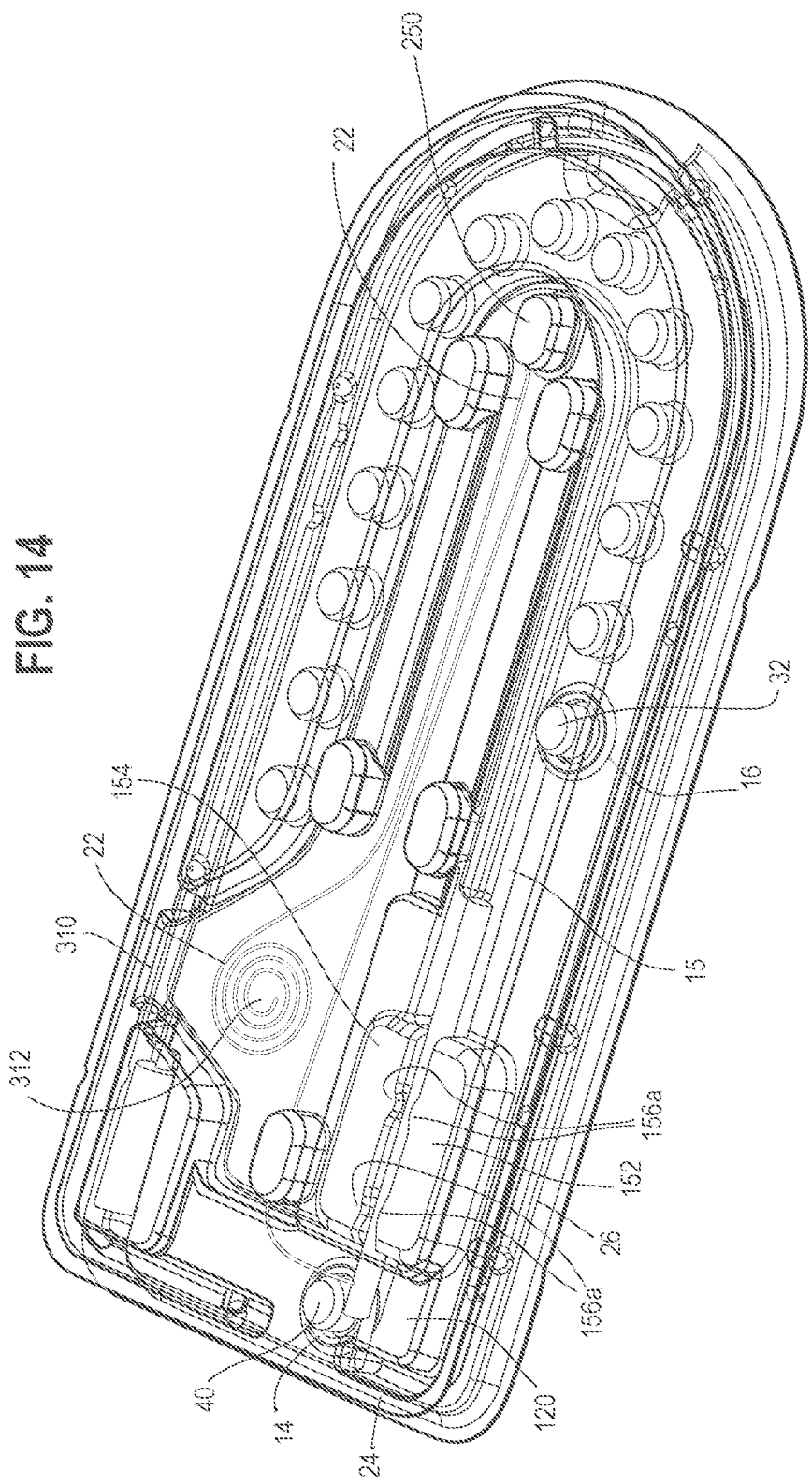
FIG. 14 is an illustration showing a perspective view of the packaging system of FIG. 13 with the tray cover placed over the tray base in accordance with certain aspects of the present disclosure.

As best shown in FIGS. 13 and 14, the tray base 26 and the tray cover (whether the hinged cover 20 or the removable cover 120) may include a space 312 for receiving an free end portion of the tether, normally after it wraps around the projection 250. The free end portion 22a may be bunched within the space 312 (shown schematically in FIG. 14), or may exit out of an opening 310 between the base 26 and tray cover, as shown in FIG. 13.

Figure 15:
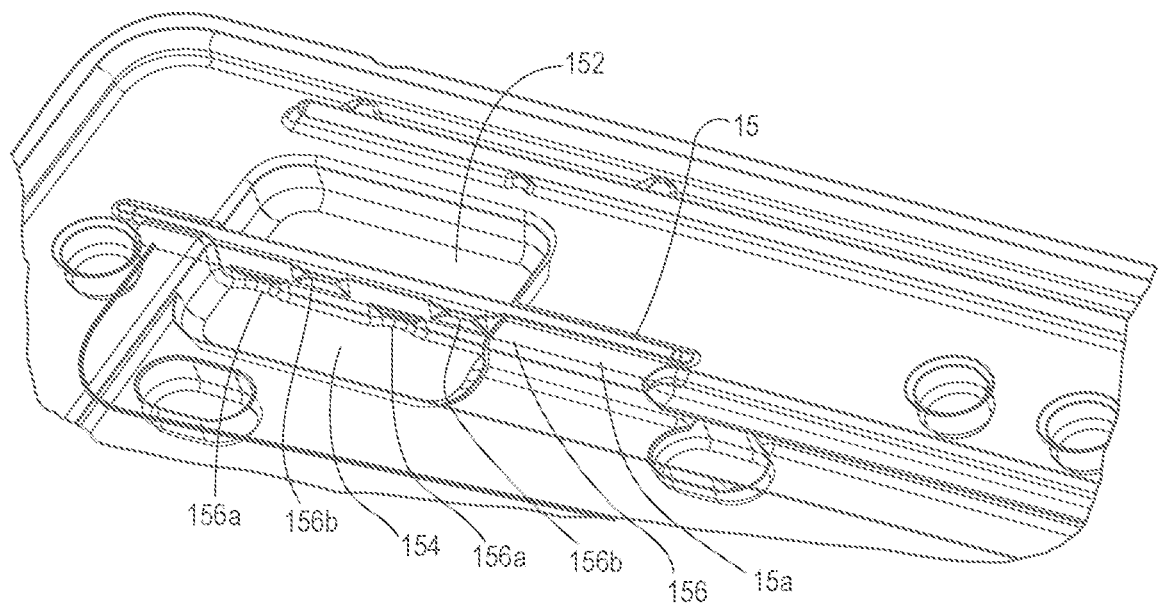
FIG. 15 is an illustration showing an enlarged bottom perspective view of a portion of the tray base of FIG. 13 in accordance with certain aspects of the present disclosure.
Figure 16:
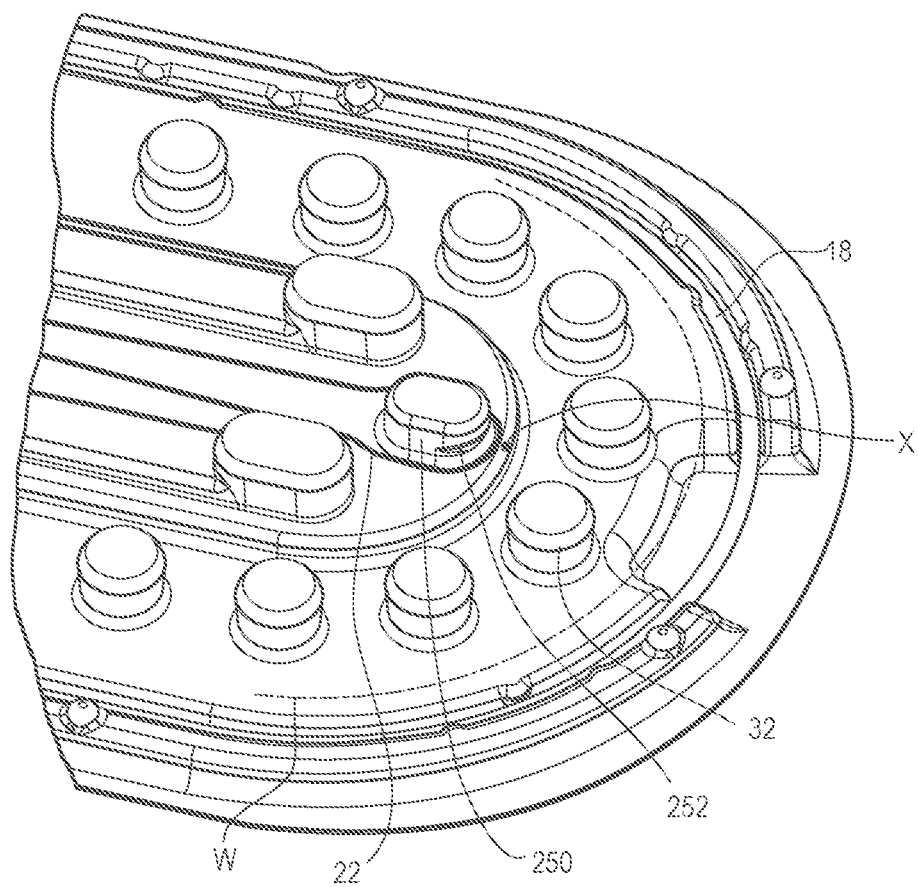
FIG. 16 is an illustration showing an enlarged top perspective of a portion of the tray base of FIG. 13 in accordance with certain aspects of the present disclosure.

In some embodiments, the tray base 26 may have a second valley 156 that is formed between third and fourth extensions 152, 154, similar to the third and fourth extensions 52, 54 discussed above. The second valley 156 is configured to receive and frictionally support and removably lock a central portion 15 of the stent therewithin. As best understood with reference to FIGS. 13 and 15, the second valley 156 is configured to receive and retain various different size (e.g. different diameters or cross-sections) elongated components, such as portions of a stent, a positioner, a dilator or other tubular component with central portions of different diameters, or for example, to retain two separate components in a stacked orientation as depicted in FIG. 13. In some embodiments, one or both of the third and fourth extensions 152, 154 may include two sets of locking features that are disposed at a different heights. A first set of locking features 156b may be disposed proximate to the floor of the tray 26, and are configured to retain a device (such as the central portion 15 disposed with respect to the first set of locking features 156a) that is of a first size (e.g. diameter or cross-sectional area_. A second set of locking features 156a may be disposed along a plane further from the floor of the tray 26 than a plane through the first set of locking features 156b, to retain a device that has a second size, which is larger than the first size (associated with a device retained by the first set of locking feature 156b). As depicted in FIG. 13 the central portion 15 has a smaller size than the tube 15a disposed in alignment with the second set of locking features 156a, which in this embodiment are disposed upon both the third and fourth extensions. FIG. 15 is a bottom perspective view and depicts the smaller central portion 15 disposed in conjunction with the first set of locking features 156b (depicted in this figure upon the fourth extension, but the locking features 156b upon the third extension would be similar), and the larger tube 15a disposed in conjunction with the second set of locking features 156b). In embodiments where the locking features 156a, 156b extend from both the third and fourth extensions 152, 154, the respective locking features may be positioned at the same relative position on the opposite extensions—to contact the retained device at the same longitudinal position, or they may be staggered—to contact the retained device at different positions from opposite sides.

The specification can be readily understood with reference to the following numbered paragraphs:

Numbered Paragraph 1: A packaging system for use with a ureteral stent comprising an elongated shaft extending between a proximal end portion and a distal end portion, comprising:
  a tray base; wherein the tray base comprising:
    a first extension disposed outwardly from a planar surface of the tray base and extending along at least a portion of a length of the tray base;
    at least one first post disposed outwardly from the planar surface of the tray base and adjacent to the first extension, wherein the at least one first post is configured to secure the distal end portion of the ureteral stent on the tray base;
    a second post disposed outwardly from the planar surface of the tray base and apart from the at least one first post by a first distance, wherein the second post is configured to secure the proximal end portion of the ureteral stent on the tray base;
    a projection disposed outwardly from the planar surface of the tray base and adjacent to the second post, wherein the projection is configured to secure a tether coupled to the proximal end portion of the ureteral stent on the tray base.

Numbered Paragraph 2: The packaging system of Numbered Paragraph 1, wherein the tray base further comprises a plurality of first posts disposed along a line that extends parallel to at least a portion of the first extension.

Numbered Paragraph 3: The packaging system of Numbered Paragraph 1, wherein spaces upon the planar surface of the tray base between the first extension and the at least one first post collectively define a first valley, wherein the first valley is configured to receive at least a portion of the elongated shaft of the ureteral stent.

Numbered Paragraph 4: The packaging system of Numbered Paragraph 1, wherein the first extension has a U shape.

Numbered Paragraph 5: The packaging system of Numbered Paragraph 1, wherein the projection comprises an under-cut structure.

Numbered Paragraph 6: The packaging system of Numbered Paragraph 1, wherein the tray base further comprises a flap hingedly mounted on the planar surface of the tray base, and wherein the flap is disposed adjacent to the projection and is configured to fit onto the projection.

Numbered Paragraph 7: The packaging system of Numbered Paragraph 1, further comprising a tray cover configured to fit onto the tray base with a ureteral stent loaded thereon.

Numbered Paragraph 8: The packaging system of Numbered Paragraph 1, further comprising a pouch configured to receive the tray base and a ureteral stent loaded thereon.

Numbered Paragraph 9: The packaging system of Numbered Paragraph 1, wherein the tray base further comprises a second extension disposed outwardly from the planar surface of the tray base and extending along at least a portion of a peripheral portion of the tray base, wherein the second extension comprises a second recess configured to receive a positioner.

Numbered Paragraph 10: The packaging system of Numbered Paragraph 1, wherein the first distance ranges from about 4 cm to about 40 cm.

Numbered Paragraph 11: The packaging system of Numbered Paragraph 1, further comprising a third extension and a fourth extension disposed outwardly from the planar surface of the tray base and adjacent to the second post, wherein the third extension and the fourth extension define a second valley therebetween on the planar surface of the tray base.

Numbered Paragraph 12: The packaging system of Numbered Paragraph 1, further comprising a first recess extending between the second post and the at least one first post.

Numbered Paragraph 13: The packaging system of Numbered Paragraph 1, further comprising a plurality of recessed cavities configured such that the tray base can be placed horizontally and securely on a support.

Numbered Paragraph 14: The packaging system of Numbered Paragraph 2, wherein the plurality of first posts are spaced along the line that extends parallel to at least a portion of the first extension.

Numbered Paragraph 15: The packaging system of Numbered Paragraph 9, wherein the at least one first post is disposed between at least a portion of the first extension and at least a portion of the second extension.

Numbered Paragraph 16: The packaging system of Numbered Paragraph 9, wherein the second extension further comprises a second notch configured for easy removal of the positioner received within the second recess.

Numbered Paragraph 17: The packaging system of Numbered Paragraph 11, wherein spaces on the planar surface of the tray base between the first valley and the second valley define a first notch configured for easy removal of the ureteral stent received within the first recess.

Numbered Paragraph 18: A packaging system for use with a ureteral stent comprising an elongated shaft extending between a proximal end portion and a distal end portion, comprising:
  a tray base; wherein the tray base comprising:
    at least one first post disposed outwardly from a planar surface of the tray base, wherein the at least one first post is configured to secure the distal end portion of the ureteral stent on the tray base;
    a second post disposed outwardly from the planar surface of the tray base and apart from the at least one first post by a first distance, wherein the second post is configured to secure the proximal end portion of the ureteral stent on the tray base;

a projection disposed outwardly from the planar surface of the tray base and adjacent to the second post, wherein the projection is configured to secure a tether coupled to the proximal end portion of the ureteral stent on the tray base.

Numbered Paragraph 19: The packaging system of Numbered Paragraph 18, wherein the tray base further comprises a flap hingedly mounted on the planar surface of the tray base, and wherein the flap is configured to fit onto the projection.

Numbered Paragraph 20: The packaging system of Numbered Paragraph 18, wherein the tray base further comprises a plurality of first posts spaced on the planar surface of the tray base so as to accommodate varying lengths of ureteral stents.

Numbered Paragraph 21: The packaging system of Numbered Paragraph 18, wherein the tray base further comprises a first recess configured to receive at least a portion of the elongated shaft of the ureteral stent.

Numbered Paragraph 22: The packaging system of Numbered Paragraph 18, further comprising a plurality of recessed cavities configured such that the tray base can be placed horizontally and securely on a support.

Numbered Paragraph 23: A packaging system for use with a ureteral stent comprising an elongated shaft extending between a proximal end portion and a distal end portion, comprising:

a tray base; wherein the tray base comprising:

at least one first post disposed outwardly from a planar surface of the tray base, wherein the at least one first post is configured to secure the distal end portion of the ureteral stent on the tray base;

a second post disposed outwardly from the planar surface of the tray base and apart from the at least one first post by a first distance, wherein the second post is configured to secure the proximal end portion of the ureteral stent on the tray base;

an extension disposed outwardly from the planar surface of the tray base, wherein the extension comprises a groove extending along at least a portion of an outer edge of the extension to releasably receive a tether of the ureteral stent therein.

Numbered Paragraph 24: The packaging system of Numbered Paragraph 23, wherein the extension comprises a notch configured to provide a passageway for the tether of the ureteral stent to extend through, such that the tether extending along the outer edge of the extension is wrapped around the at least one first post.

Numbered Paragraph 25: The packaging system of Numbered Paragraph 23, further comprising a plurality of recessed cavities configured such that the tray base can be placed horizontally and securely on a support.

While various embodiments of the present disclosure have been described, the present disclosure is not to be restricted except in light of the attached claims and their equivalents. One skilled in the relevant art will recognize that numerous variations and modifications may be made to the embodiments described above without departing from the scope of the present invention, as defined by the appended claims. Moreover, the advantages described herein are not necessarily the only advantages of the present disclosure and it is not necessarily expected that every embodiment of the present disclosure will achieve all of the advantages described.

We claim:

1. A packaging system for use with an elongate medical device comprising an elongated shaft extending between a proximal end portion and a distal end portion, comprising:
   a tray base, wherein the tray base comprises:
      a plurality of first posts disposed outwardly with respect to a planar surface of the tray base; and
      a second post disposed outwardly with respect to the planar surface of the tray base and apart from the plurality of first posts, wherein the second post is configured to secure one end portion of a proximal end portion or a distal end portion of an elongate medical device on the tray base by wrapping the one end portion around the second post,
      wherein each first post of the plurality of first posts is configured to secure the other end portion of a proximal end portion or a distal end portion of an elongate medical device on the tray base by wrapping the other end portion around the first post,
      wherein the plurality of first posts is disposed along a U-shaped line,
      wherein the tray base further comprises a pair of extensions disposed outwardly with respect to the planar surface of the tray base, and the pair of extensions defines a valley therebetween, and
      wherein the valley is disposed between the second post and at least one of the plurality of first posts, and the valley is configured to receive and frictionally support an elongate medical device therein.

2. The packaging system of claim 1, wherein the tray base further comprises a flap hingedly mounted on the planar surface of the tray base, and wherein the flap is configured to fit onto the projection.

3. The packaging system of claim 1, wherein the plurality of first posts are spaced on the tray base so as to accommodate varying lengths of elongate medical devices.

4. The packaging system of claim 1, wherein the tray base further comprises a first recess configured to receive at least a portion of an elongated shaft of an elongate medical device.

5. The packaging system of claim 1, wherein the tray base further comprises a projection disposed outwardly with respect to the planar surface of the tray base, and wherein the projection is configured to secure a tether coupled to one end portion of a proximal end portion or a distal end portion of an elongate medical device on the tray base.

6. The packaging system of claim 5, wherein the projection comprises an under-cut structure.

7. The packaging system of claim 1, further comprising a tray cover configured to fit onto the tray base with an elongate medical device loaded thereon.

8. The packaging system of claim 7, wherein when the tray cover is placed over the tray base, a space is formed therebetween, and wherein the space is configured to receive a free end portion of a tether coupled to one end portion of a proximal end portion or a distal end portion of an elongate medical device on the tray base.

9. The packaging system of claim 7, wherein when the tray cover is placed over the tray base, an opening is formed therebetween, and wherein the opening is configured such that a free end portion of a tether coupled to one end portion of a proximal end portion or a distal end portion of an elongate medical device on the tray base can exit out of the opening.

10. The packaging system of claim 1, wherein the valley is configured to receive and frictionally support elongated components with different sizes therein.

11. The packaging system of claim 1, wherein one or both of the pair of extensions include first and second pairs of locking features that are disposed at different heights above the planar surface of the tray base.

12. The packaging system of claim 11, wherein the first pair of locking features is disposed closer to the planar surface of the tray base than the second pair of locking features.

13. The packaging system of claim 11, wherein the first pair of locking features is configured to receive an elongated component with a first size, and wherein the second pair of locking features is configured to receive an elongated component with a second size.

14. The packaging system of claim 13, wherein the first size is smaller than the second size.

15. The packaging system of claim 1, further comprising an elongate medical device,
- wherein one end portion of a proximal end portion or a distal end portion of the elongate medical device is secured to a first post of the plurality of first posts; and
- wherein the other end portion of a proximal end portion or a distal end portion of the elongate medical device is secured to the second post.

16. The packaging system of claim 1, wherein the second post is disposed nearer to a second end of the tray base than to the plurality of first posts, and the plurality of first posts is nearer to a first end of the tray base that is different than the second end of the tray base.

* * * * *